United States Patent [19]

Yonekura et al.

[11] Patent Number: 4,892,726

[45] Date of Patent: Jan. 9, 1990

[54] MAKEUP OR COSMETIC COMPOSITIONS

[75] Inventors: Kazuya Yonekura; Shoji Daikuzono, both of Tokyo, Japan

[73] Assignee: Toshiba Silicon Co., Ltd., Japan

[21] Appl. No.: 196,917

[22] Filed: May 20, 1988

[30] Foreign Application Priority Data

May 29, 1987 [JP] Japan ................ 62-131349

[51] Int. Cl.⁴ .................. A61K 7/21; A61K 7/35; A61K 7/2
[52] U.S. Cl. ................................ 424/63; 424/69
[58] Field of Search .................... 429/63, 69

[56] References Cited

U.S. PATENT DOCUMENTS 4,528,390  7/1985  Kimurz ...................... 528/21 X

FOREIGN PATENT DOCUMENTS 245815   5/1987  Fed. Rep. of Germany .
098205   6/1982  Japan ........................ 424/69
100514   5/1986  Japan ........................ 424/69
194009   8/1986  Japan .
1141994  of 1909 United Kingdom ........ 424/69

Primary Examiner—Ellis P. Robinson
Assistant Examiner—Susan S. Rucker

[57] ABSTRACT

There are disclosed makeup or cosmetic compositions comprising polymethylsilsesquiozane powders.

3 Claims, No Drawings

MAKEUP OR COSMETIC COMPOSITIONS

The present application claims the priority of Japanese Pat. Application Ser. No. 62-131349 filed on May 29, 1987

BACKGROUND OF THE INVENTION

1. Field of the Invention

The present invention relates to makeup and cosmetic compositions. More particularly, the present invention relates to makeup and cosmetic compositions which provide for smooth application and are pleasant to the touch.

2. Statement of the Prior Art

In general, makeup and cosmetic compositions are basically composed of components such as oils, powders, water soluble bases, etc. Further, such composition come in a variety of forms such as a solid foundation, including solid eye shadows and lipsticks, or liquid emulsion type and cream emulsion type foundations, etc.

A variety of powders are used in makeup and cosmetic compositions for art known purposes. Talc, kaolin, zinc white, titanium white, calcium carbonate or magnesium carbonate are effectively employed as loading pigments. Inorganic pigments include titanium white, zinc white, carbon black, iron tetratrioxide, yellow ocher, red iron oxide, amber, ultramarine, etc. Organic pigments having a strong coloring property are also employed in powder form Additional powders generally employed in makeup and cosmetic compositions include zinc stearate, magnesium stearate, starch, silica powders, bentonite, etc.

As the prior art using specific powder components, there are known cosmetic compositions in which organic synthetic resin powders are incorporated as loading pigments or modifiers to improve clearness of hue, coloring, transparency, etc. (cf. Published Unexamined Japanese Patent Application No. 99236/1977). Also known are cosmetic compositions in which organo-polysiloxane cured powders obtained by grinding an organo-polysiloxane elastomer or organo-polysiloxane resin are used to improve application (cf. Published Unexamined Japanese Patent Application No. 194009/1986). However, in the former case, it is desirable to improve the natural appearance of the color In the latter case, the cured rubber or resin is pulverized to a powder having an irregular broad particle size distribution which is too broad and is extremely difficult to control Thus, smoothness of makeup or cosmetic compositions containing these powders upon application is insufficient.

SUMMARY OF THE INVENTION

An object of the present invention is to provide makeup or cosmetic compositions which eliminate the foregoing problems in the prior art and can provide extreme smoothness upon application and impart natural color.

As a result of extensive investigations to achieve the object described above, the present inventors have found that by using polymethylsilsesquioxane powders as a powder component of makeup or cosmetic compositions, excellent effects of natural color and smoothness upon application, are gained. Thus, the present invention relates to makeup or cosmetic compositions characterized by containing polymethylsilsesquioxane powders.

DETAILED DESCRIPTION OF THE INVENTION

Polymethylsilsesquioxane powders are the characteristic component in the present invention that contribute to smooth application of makeup or cosmetic compositions to the skin, to a moisturized feeling and to more enhanced functions of pigment powders used as a cosmetic component in combination therewith.

Such polymethylsilsesquioxane powders can be obtained by any of several methods. There is a method which comprises either hydrolyzing methyl trichlorosilane while spraying it or dropwise adding methyl trichlorosilane in large amounts of water to cause hydrolysis and condensation (cf. Belgian Patent No. 572,412). There is a method which comprises hydrolyzing and condensing methyl trialkoxysilanes, etc. in an aqueous solution containing alkali metal carbonates or alkaline earth metal hydroxides (cf. Published Unexamined Japanese Patent Application No. 72300/1979). There is also a method which comprises hydrolyzing and condensing methyl trialkoxysilanes, etc. in an aqueous solution of ammonia or amines (cf Published Unexamined Japanese Patent Application No. 13813/1985), etc. Of these methods, the polymethylsilsesquioxane powders obtained by the method of Published Unexamined Japanese Patent Application No. 13813/1985 is preferred to achieve the object of the present invention, because the powders have a small chlorine content, are free from alkali metals or alkaline earth metals and have excellent free fluidity In addition and regardless of the method of manufacture, it is preferred that the shape of the polymethylsilsesquioxane powders be independent and substantially spherical and that more than 80% of the whole particles be within the range of ±30% of a mean particle diameter in the particle size distribution.

The mean particle diameter of the polymethylsilsesquioxane powders is preferably 0.05 to 100 $\mu$m, more preferably 0.1 to 20 $\mu$m. In case that the particle diameter is too small, it is difficult to prepare them. Further in case that the particle diameter is too large, it is not only difficult to prepare but also it is difficult to achieve the object of the present invention The amount of the polymethylsilsesquioxane powders to be formulated can vary depending upon the form of the particular cosmetic under manufacture and is not particularly limited However, it is preferred that the powders be incorporated, for example, in the case of press type makeup cosmetic compositions, in the range of from 1 to 60 wt% and, in the case of liquid makeup cosmetic compositions in the range of from 0.1 to 40 wt%.

The makeup cosmetic composition of the present invention can be prepared by formulating the polymethylsilsesquioxane powders and other cosmetic powdery raw materials in cosmetic binder oil and dispersing them homogeneously. As the other cosmetic powdery raw materials, there can be used loading pigments such as talc, kaolin, zinc white, magnesium carbonate, calcium carbonate, silica powders, starch, metal salts of higher fatty acid, silk powders, bentonite, etc.; inorganic pigments having various colors such as titanium white, zinc white, carbon black, iron tetratrioxide, yellow ocher, red iron oxide, amber, ultramarine, etc.; organic color pigments such as tar pigment, 62-carotin, safflower pigment, chlorophile, cochineal, etc.; and pearl pigments such as mica titanium, etc.

As the cosmetic binder oil, there can be used those conventionally employed, for example, liquid paraffin, vaseline, beeswax, microcrystalline wax, olive oil, stearic acid, castor oil; higher alcohols such as octyl alcohol, hexadecyl alcohol, etc.; lower alcohols such as ethanol, etc.; esters, higher fatty acids, etc. In addition, there may also be used siloxanes such as polydimethylsiloxane, polymethylphenylsiloxane, etc.

If necessary, water, surface-active agents, perfume, thickeners, antiseptics, etc. can also be formulated in the makeup or cosmetic composition of the present invention.

The makeup or cosmetic composition of the present invention contains the polymethylsilsesquioxane powders and can thus provide an extremely smooth application and impart favorable natural color.

EXAMPLES OF THE INVENTION

Hereafter the present invention will be described with reference to the examples, wherein "parts" are "parts by weight∞.

Synthesis Example 1

In a four-necked flask equipped with a thermometer, a reflux condenser and stirrer, 500 parts of water and 50 parts of 28% ammonium aqueous solution were charged. Then, 200 parts of methyl trimethoxysilane were added dropwise to the ammonia aqueous solution over 40 minutes with stirring The reaction temperature started from 10° C and reached 30° C upon completion of the dropwise addition Next, the system was heated with a mantle heater to reflux at 84° C Stirring was continued for about an hour at this temperature. After cooling, the precipitated product in the flask was collected, washed with water and dried Then, via a pulverizing step, polymethylsilsesquioxane powders having a mean particle diameter of 2 μm, having a particle diameter of 1.7 to 2.1 μm in more than 99% of the whole particles and having excellent free fluidity were obtained

Synthesis Example 2

In a four-necked flask equipped with a thermometer, a reflux condenser and stirrer, 4,000 parts of water and 50 parts of 28% ammonium aqueous solution were charged The mixture was stirred at 100 r.p.m for 10 minutes to make a homogeneous ammonia aqueous solution Then, 600 parts of methyl trimethoxysilane having a chlorine content of 10 ppm calculated as a chlorine atom were rapidly added to the ammonia aqueous solution, while rotating the stirrer at 5 r.p.m., to form two phases The methyl trimethoxysilane phase formed the upper layer and the ammonia aqueous solution phase formed the lower layer Then, the stirring rate of the stirrer was changed to 20 r.p.m. and hydrolysis and condensation were allowed to proceed at the interface between the methyl trimethoxysilane and the ammonia aqueous solution, while maintaining the two phase state. As the reaction proceeded, the reaction product gradually precipitated in the lower layer The lower layer turned white and became turbid because of the suspension of the reaction product The methyl trimethoxysilane phase in the upper layer became thinner and disappeared in about 3 hours (confirmed by observation with the eye). Subsequently, the temperature was maintained at 50° to 60° C and the system was stirred for 3 hours under the same conditions Thereafter, the system was cooled to 25° C Then, after the precipitated product was filtered through a wire gauze of 100 mesh, it was centrifuged to dehydrate, whereby the product was rendered cake like. The cake phase was dried in an oven of 200° C and crushed using a labo jet to give white powders of polymethylsilsesquioxane The thus obtained polymethylsilsesquioxane powders were substantially spherical and had a mean particle diameter of about 1.9 μm.

Synthesis Example

Spherical polymethylsilsesquioxane powders having a mean particle diameter of about 4.5 μm were obtained in a manner similar to Synthesis Example 1 except that the amount of 28% ammonium aqueous solution was changed to 5 parts and the stirring rate after the system was rendered two phase state was changed to 25 r.p.m.

EXAMPLE 1

In Container (1) were charged 30 parts of talc, 5 parts of kaolin, 25 parts of sericite, 10 parts of titanium dioxide and 1 part of red iron oxide. While homogeneously mixing them, the mixture was heated at 100° C for 2 hours. In the mixture were formulated 5 parts of polymethylsilsesquioxane powders obtained in Synthesis Example 1 and 5 parts of polyethylene powders. While further pulverizing, they were homogeneously mixed.

On the other hand, 3 parts of polydimethylsioloxane having a viscosity of 100 cSt at 25° C, 4 parts of liquid paraffin, 3 parts of stearyl alcohol, 2 parts of beeswax and 2 parts of squalane were charged in another Container (2). Then the mixture was heated at 100° C for an hour to dissolve homogeneously. Thereafter, the contents of Container (1) and Container (2) were combined and mixed homogeneously. After pulverizing, press molding was performed to give a cosmetic foundation.

EXAMPLES 2 and 3

Two kinds of foundations were obtained in a manner similar to Example 1 except that 5 parts of spherical polymethylsilsesquioxane powders obtained in Synthesis Examples 2 and 3, respectively were used instead of 5 parts of polymethylsilsesquioxane powders obtained in Synthesis Example 1

COMPARATIVE EXAMPLES 1

A foundation was obtained in a manner similar to Example 1 except that 5 parts of polyethylene powders were used instead of 5 parts of polymethylsilsesquioxane powders.

SYNTHESIS EXAMPLE 4

A mixture of 100 parts of polysiloxane composed of a dimethylsiloxane units end-stopped with dimethylvinylsilyl groups and having a viscosity of 500 cSt at 25° C. with 3.5 parts of polymethylhydrogensiloxane end-stopped with trimethylsilyl groups and having a viscosity of 20 cSt at 25° C was mixed with chloroplatinic acid in an amount of 10 ppm as platinum metal based on the total amount of the mixture and isopropyl alcohol solution The mixture was heated at 150° C for 2 hours to give rubbery cured product The cured product was ground into fine powders with an atomizer to give powders having a particle diameter of 1 to 50 μm.

COMPARATIVE EXAMPLE 2

A foundation was obtained in a manner similar to Example 1 except that 5 parts of the powders of Synthesis Example 4 described above were used instead of 5 parts of polymethylsilsesquioxane powders obtained in Synthesis Example 1. Evaluation test With respect to the 5 cosmetic of foundations obtained in the examples and comparative examples, a use test by application was performed by 10 female panel members. The results are shown in Table 1. Evaluation standards are as follows. Indication is by a mean value.

Extremely good =3, Good =2, Ordinary =1

TABLE 1

|  | Example | | | Comparative Example | |
|---|---|---|---|---|---|
|  | 1 | 2 | 3 | 1 | 2 |
| Spreadability | 2.1 | 2.9 | 2.8 | 1.6 | 2.0 |
| Appearance (color) | 2.8 | 2.9 | 2.9 | 1.5 | 1.7 |
| Feel of application | 2.5 | 3.0 | 3.0 | 1.1 | 1.6 |

As is evident from the table, the cosmetic compositions of the present invention were evaluated to be extremely good or good.

While the invention has been described in detail and with reference to specific embodiments thereof, it is apparent to one skilled in the art that various changes and modifications can be made therein without departing from the spirit and the scope of the present invention.

What is claimed is:

1. A makeup or cosmetic composition comprising polymethylsilsesquioxane powders which has a mean particle diameter of 0.05 to 100 μm and where 80% or more of the polymethylsilsesquioxane particles are within the range of ±30% of the mean particle diameter.

2. A makeup or cosmetic composition as claimed in claim 1 wherein polymethylsilsesquioxane powders are spherical.

3. A makeup or cosmetic composition as claimed in claim 1 further comprising cosmetic binder oil.

* * * * *